United States Patent
Cerreti et al.

(10) Patent No.: US 9,326,944 B2
(45) Date of Patent: May 3, 2016

(54) FREEZE-DRIED FORMULATIONS OF FGF-18

(75) Inventors: Alessandra Cerreti, Rome (IT);
Alessandra Del Rio, Rome (IT)

(73) Assignee: ARES TRADING S.A., Aubonne (CH)

( * ) Notice: Subject to any disclaimer, the term of this patent is extended or adjusted under 35 U.S.C. 154(b) by 0 days.

(21) Appl. No.: 14/126,937

(22) PCT Filed: Jun. 15, 2012

(86) PCT No.: PCT/EP2012/061495
§ 371 (c)(1),
(2), (4) Date: Dec. 17, 2013

(87) PCT Pub. No.: WO2012/172072
PCT Pub. Date: Dec. 20, 2012

(65) Prior Publication Data
US 2014/0121162 A1    May 1, 2014

Related U.S. Application Data

(60) Provisional application No. 61/499,216, filed on Jun. 21, 2011.

(30) Foreign Application Priority Data

Jun. 17, 2011 (EP) .................................. 11170437

(51) Int. Cl.
*A61K 38/18* (2006.01)
*A61K 9/19* (2006.01)

(52) U.S. Cl.
CPC . *A61K 9/19* (2013.01); *A61K 38/18* (2013.01); *A61K 38/1825* (2013.01)

(58) Field of Classification Search
None
See application file for complete search history.

(56) References Cited

U.S. PATENT DOCUMENTS

| | | | | |
|---|---|---|---|---|
| 5,217,954 A | * | 6/1993 | Foster | C07K 14/503 514/9.1 |
| 5,989,866 A | * | 11/1999 | Deisher et al. | 435/69.4 |
| 8,765,124 B2 | | 7/2014 | Saito et al. | |
| 2001/0056066 A1 | * | 12/2001 | Bugelski et al. | 514/8 |
| 2003/0113316 A1 | | 6/2003 | Kaisheva et al. | |
| 2005/0220758 A1 | * | 10/2005 | Zobel | A61K 9/0019 424/85.1 |
| 2006/0172384 A1 | * | 8/2006 | Reardon et al. | 435/69.1 |

FOREIGN PATENT DOCUMENTS

| | | |
|---|---|---|
| JP | 2009-526080 | 8/2007 |
| WO | WO 92/01442 A1 * | 2/1992 |
| WO | WO 97/04801 | 2/1997 |
| WO | WO 02/17956 | 3/2002 |
| WO | WO 2004/075913 | 9/2004 |
| WO | WO 2007/076354 | 7/2007 |
| WO | WO 2007/092829 | 8/2007 |
| WO | WO 2008/121563 | 10/2008 |

OTHER PUBLICATIONS

Avis KE. "Parenteral Preparations," Chapter 85, in Remington's Pharmaceutical Sciences, 17th edition (Jun. 1985), Mack Pub. Co., Easton, Pennsylvania, pp. 1518, 1538, 1539.*
Wang W. Lyophilization and development of solid protein pharmaceuticals. Int J Pharm. Aug. 10, 2000;203(1-2):1-60.*
Ellsworth, J. L. et al. "Fibroblast growth factor-18 is a trophic factor for mature chondrocytes and their progenitors" *Osteoarthritis and Cartilage*, 2002, pp. 308-320, vol. 10.
Custers, R. J. H. et al. "Reliability, reproducibility and variability of the traditional Histologic/Histochemical Grading System vs the new OARSI Osteoarthritis Cartilage Histopathology Assessment System" *Osteoarthritis and Cartilage*, 2007, pp. 1241-1248, vol. 15.
Shimoaka, T. et al. "Regulation of Osteoblast, Chondrocyte, and Osteoclast Functions by Fibroblast Growth Factor (FGF)-18 in Comparison with FGF-2 and FGF-10*" *The Journal of Biological Chemistry*, Mar. 1, 2002, pp. 7493-7500, vol. 277, No. 9.

* cited by examiner

*Primary Examiner* — David Romeo
(74) *Attorney, Agent, or Firm* — Saliwanchik, Lloyd & Eisenschenk

(57) ABSTRACT

The invention relates to the field of pharmaceutical formulations. More particularly it is directed to freeze-dried formulations of Fibroblast Growth Factor 18 (FGF-18) compound and to methods of producing such formulations. The freeze-dried formulations according to the invention are stable upon storage for an appropriate period of time. They can be used, after reconstitution, for the treatment of cartilage disorders such as osteoarthritis or cartilage injury.

12 Claims, 1 Drawing Sheet

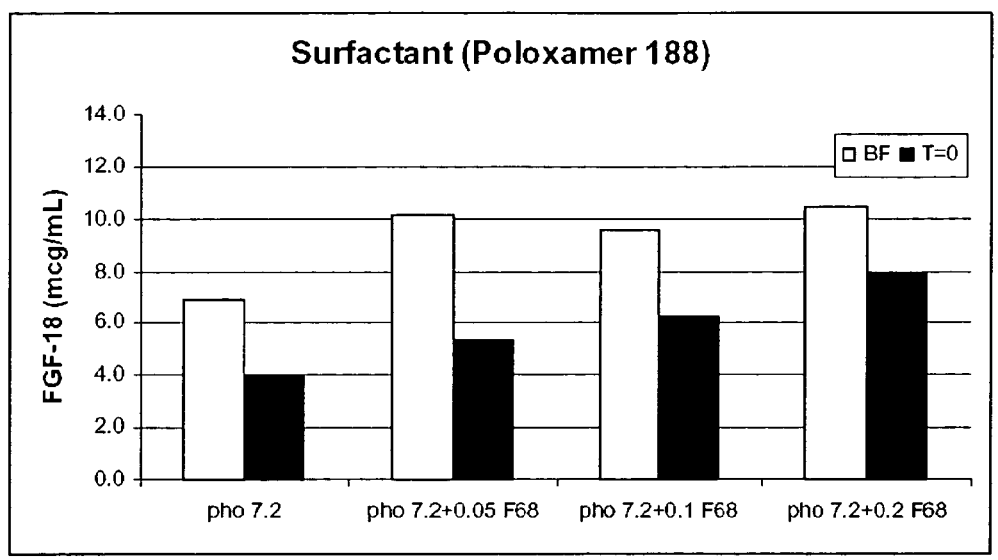

SEQUENCE LISTING

<160> NUMBER OF SEQ ID NOS: 2

<210> SEQ ID NO 1

```
<211> LENGTH: 207
<212> TYPE: PRT
<213> ORGANISM: Homo sapiens
<220> FEATURE:
<223> OTHER INFORMATION: human FGF-18

<400> SEQUENCE: 1

Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
                20                  25                  30

Phe Arg Ile His Val Glu Asn Gln Thr Arg Ala Arg Asp Asp Val Ser
                35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
                100                 105                 110

Lys Gly Lys Leu Val Gly Lys Pro Asp Gly Thr Ser Lys Glu Cys Val
                115                 120                 125

Phe Ile Glu Lys Val Leu Glu Asn Asn Tyr Thr Ala Leu Met Ser Ala
                130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
                180                 185                 190

Thr Val Thr Lys Arg Ser Arg Arg Ile Arg Pro Thr His Pro Ala
                195                 200                 205

<210> SEQ ID NO 2
<211> LENGTH: 170
<212> TYPE: PRT
<213> ORGANISM: Artificial
<220> FEATURE:
<223> OTHER INFORMATION: recombinant truncated FGF-18(trFGF-18)

<400> SEQUENCE: 2

Met Glu Glu Asn Val Asp Phe Arg Ile His Val Glu Asn Gln Thr Arg
1               5                   10                  15

Ala Arg Asp Asp Val Ser Arg Lys Gln Leu Arg Leu Tyr Gln Leu Tyr
                20                  25                  30

Ser Arg Thr Ser Gly Lys His Ile Gln Val Leu Gly Arg Arg Ile Ser
                35                  40                  45

Ala Arg Gly Glu Asp Gly Asp Lys Tyr Ala Gln Leu Leu Val Glu Thr
    50                  55                  60

Asp Thr Phe Gly Ser Gln Val Arg Ile Lys Gly Lys Glu Thr Glu Phe
65                  70                  75                  80

Tyr Leu Cys Met Asn Arg Lys Gly Lys Leu Val Gly Lys Pro Asp Gly
                85                  90                  95

Thr Ser Lys Glu Cys Val Phe Ile Glu Lys Val Leu Glu Asn Asn Tyr
                100                 105                 110

Thr Ala Leu Met Ser Ala Lys Tyr Ser Gly Trp Tyr Val Gly Phe Thr
```

-continued

```
            115                 120                 125
Lys Lys Gly Arg Pro Arg Lys Gly Pro Lys Thr Arg Glu Asn Gln Gln
        130                 135                 140

Asp Val His Phe Met Lys Arg Tyr Pro Lys Gly Gln Pro Glu Leu Gln
145                 150                 155                 160

Lys Pro Phe Lys Tyr Thr Thr Val Thr Lys
                165             170
```

FREEZE-DRIED FORMULATIONS OF FGF-18

CROSS-REFERENCE TO RELATED APPLICATIONS

This application is the U.S. national stage application of International Patent Application No. PCT/EP2012/061495, filed Jun. 15, 2012, which claims the benefit of U.S. Provisional Patent Application No. 61/499,216, filed Jun. 21, 2011.

FIELD OF INVENTION

The invention relates to the field of pharmaceutical formulations. More particularly it is directed to freeze-dried formulations of Fibroblast Growth Factor 18 (FGF-18) protein and to methods of producing such formulations. The freeze-dried formulations according to the invention are stable upon storage at room temperature for an appropriate period of time.

BACKGROUND OF THE INVENTION

Fibroblast Growth factor 18 (FGF-18) is a member of the Fibroblast Growth Factor (FGF) family of proteins, closely related to FGF-8 and FGF-17. Members of the FGF family are characterized by heparin binding domains. Such a putative heparin-binding domain has been identified for FGF-18. It is postulated that receptor-mediated signalling is initiated upon binding of FGF ligand complexed with cell-surface heparin sulfate proteoglycans.

It has been shown that FGF-18 is a proliferative agent for chondrocytes and osteoblasts (Ellsworth et al., 2002, Osteoarthritis and Cartilage, 10: 308-320; Shimoaka et al., 2002, J. Bio. Chem. 277(9):7493-7500). FGF-18 has been proposed for the treatment of cartilage disorder such as osteoarthritis and cartilage injury either alone (WO2008/023063) or in combination with hyaluronic acid (WO2004/032849).

Pharmaceutical compositions comprising an FGF polypeptide are known from the art. WO00/21548 discloses pharmaceutical compositions comprising a recombinant FGF in combination with a pharmaceutically acceptable carrier or diluent. Examples of suitable carriers or diluents for injectable solutions include water or isotonic saline solutions.

WO2008/121563 is related to pharmaceutical formulations comprising an FGF-21 compound prepared in a unit dosage injectable form together with a pharmaceutically acceptable carrier. Suitable carrier might be, among others, a sugar, a buffer and/or a surfactant.

WO92/01442 discloses a lyophilized composition comprising a FGF, a pharmaceutically acceptable bulking agent and either i) an alkali metal salt of cellulose or ii) a combination of polyoxyethylene sorbitan fatty acid ester with cysteine. The components of i) and ii) allow the FGF composition to be stabilized.

WO01/39788 describes pharmaceutical compositions comprising an FGF-18 compound together with a cytotoxin, in a mixture with a pharmaceutically acceptable carrier, e.g. phosphate-buffered saline.

WO2008/023063 discloses formulations comprising an FGF-18 compound together with at least one pharmaceutically acceptable carrier, excipients, or the like. As an example, it discloses a formulation for injection comprising FGF-18 in vehicles such as saline, dextrose solution, serum albumin and Ringer's solution.

When preparing a pharmaceutical composition comprising a bioactive protein, said composition must be formulated in such a way that the activity of the protein is maintained for an appropriate period of time. A loss in activity/stability of the protein may result from chemical or physical instabilities of the protein notably due to denaturation, aggregation or oxidation. The resulting products may thus be pharmaceutically unacceptable. Although the use of excipient(s) is known to increase the stability of a given protein, the stabilizing effects of these excipients is highly dependent of the nature of the excipients and of the bioactive protein itself.

There remains a need for further formulations containing FGF-18 as an active ingredient, wherein said formulations are stable for an appropriate period of time and suitable for use in injection, preferably for intraarticular injection. Said formulations could be useful for administration in the treatment of a cartilage disorder in a patient, such as osteoarthritis or cartilage injury.

SUMMARY OF THE INVENTION

It is an object of the present invention to provide a novel formulation containing an FGF-18 protein. More particularly, said formulation is a stable freeze-dried (or lyophilized) formulation containing FGF-18. The invention also provides methods for preparing the freeze-dried formulation according to the present invention. The freeze-dried formulation herein described may be useful, after reconstitution, for administration in the treatment of cartilage disorders.

In a first aspect, the invention provides a stable freeze-dried formulation comprising or consisting of FGF-18, a buffer, a poloxamer surfactant and a sugar as stabilizing agent. In a preferred embodiment, the buffer is a phosphate buffer, the poloxamer surfactant is poloxamer 188, and the stabilizing agent is sucrose. In a further preferred embodiment the buffer keeps the pH at or about 6 to 8, and more particularly at or about 7.2. In a further preferred embodiment, the concentration of the poloxamer surfactant is at or about 0.1 to 0.4 mg/vial. Preferably, FGF-18 is selected from the group consisting of: 1) a polypeptide comprising or consisting of the mature form of human FGF-18, corresponding to the sequence comprising or consisting of residue 28 (Glu) to residue 207(Ala) of SEQ ID NO: 1, 2) a polypeptide comprising or consisting of a truncated form of human FGF-18 comprising or consisting of residue 28 (Glu) to residue 196 (Lys) of SEQ ID NO:1, and 3) a polypeptide comprising or consisting of SEQ ID NO:2. More preferably, FGF-18 is trFGF-18, as defined hereafter.

In a second aspect, the invention provides a method for manufacturing a stable freeze-dried formulation of FGF-18, comprising the steps of:
1) forming a mixture of FGF-18, together with a buffer, a surfactant and a stabilizing agent, and
2) subjecting the mixture to lyophilisation (freeze-drying), wherein the buffer is a phosphate buffer, the stabilizing agent is a sugar, such as sucrose, and the surfactant is a poloxamer surfactant, such as poloxamer 188. In a preferred embodiment the buffer keeps the pH at or about 6 to 8, and more particularly at or about 7.2. Preferably, FGF-18 is selected from the group consisting of: 1) a polypeptide comprising or consisting of the mature form of human FGF-18, corresponding to the sequence comprising or consisting of residue 28 (Glu) to residue 207(Ala) of SEQ ID NO: 1, 2) a polypeptide comprising or consisting of a truncated form of human FGF-18 comprising or consisting of residue 28 (Glu) to residue 196 (Lys) of SEQ ID NO:1, and 3) a polypeptide comprising or consisting of SEQ ID NO:2. More preferably, FGF-18 is trFGF-18, as defined hereafter.

In a third aspect, the invention provides an article of manufacture for pharmaceutical or veterinary use, comprising:

1) a first container comprising a stable freeze-dried formulation, said freeze-dried formulation comprising FGF-18, a buffer, a surfactant and a stabilizing agent, and 2) a second container comprising a solvent for reconstitution, wherein the buffer is a phosphate buffer, the stabilizing agent is a sugar, such as sucrose, the surfactant is a poloxamer surfactant, such as poloxamer 188, and the solvent for reconstitution is water or a saline solution (e.g. 0.9% w/v sodium chloride for injection). Preferably, FGF-18 is selected from the group consisting of: 1) a polypeptide comprising or consisting of the mature form of human FGF-18, corresponding to the sequence comprising or consisting of residue 28 (Glu) to residue 207(Ala) of SEQ ID NO: 1, 2) a polypeptide comprising or consisting of a truncated form of human FGF-18 comprising or consisting of residue 28 (Glu) to residue 196 (Lys) of SEQ ID NO:1, and 3) a polypeptide comprising or consisting of SEQ ID NO:2. More preferably, FGF-18 is trFGF-18, as defined hereafter.

DEFINITIONS

The term "FGF-18 protein" or "FGF-18", as used herein, is intended to be a protein maintaining at least one biological activity of the human FGF-18 protein. FGF-18 may be native, in its mature form, or a truncated form thereof. Biological activities of the human FGF-18 protein include notably the increase in osteoblastic activity (see WO98/16644) or in cartilage formation (see WO2008/023063).

Native, or wild-type, human FGF-18 is a protein expressed by chondrocytes of articular cartilage. Human FGF-18 was first designated zFGF-5 and is fully described in WO98/16644. SEQ ID NO:1 corresponds to the amino acid sequence of the native human FGF-18, with a signal peptide consisting of amino acid residues 1(Met) to 27(Ala). The mature form of human FGF-18 corresponds to the amino acid sequence from residue 28 (Glu) to residue 207(Ala) of SEQ ID NO: 1 (180 amino acids). FGF-18 has specificity for FGFR4 and the "IIIc" splice variants of FGFR3 and FGFR2 (Ellsworth et al., 2002, Osteoarthritis and Cartilage, 10: 308-320). The mature form of FGF-18 has an average mass of 21.04 kDa.

FGF-18, in the present invention, may be produced by recombinant method, such as taught by the application WO2006/063362. Depending on the expression systems and conditions, FGF-18 in the present invention is expressed in a recombinant host cell with a starting Methionine (Met residue) or with a signal sequence for secretion. When expressed in prokaryotic host, such as in *E. coli*, FGF-18 contains an additional Met residue in N-terminal of its sequence. For instance, the amino acid sequence of human FGF-18, when expressed in *E. coli*, starts with a Met residue in N-term (position 1) followed by residues 28 (Glu) to residue 207 (Ala) of SEQ ID NO: 1.

The term "truncated form" of FGF-18, as used herein, refers to a protein which comprises or consists of residues 28 (Glu) to 196 (Lys) of SEQ ID NO: 1. Preferably, the truncated form of FGF-18 protein is the polypeptide designated "trFGF-18" (170 amino acids), which starts with a Met residue (in N-terminal) followed by amino acid residues 28 (Glu)-196 (Lys) of the wild-type human FGF-18. The amino acid sequence of trFGF-18 is shown in SEQ ID NO:2 (amino acid residues 2 to 170 of SEQ ID NO:2 correspond to amino acid residues 28 to 196 of SEQ ID NO:1). trFGF-18 is a recombinant truncated form of human FGF-18, produced in *E. coli* (see WO2006/063362). trFGF-18 has been shown to display similar activities as the mature human FGF-18, e.g. it increases chondrocyte proliferation and cartilage deposition leading to repair and reconstruction for a variety of cartilaginous tissues (see WO2008/023063). trFGF-18, has an average mass of 19.83 kDa.

The term "stability", as used herein, refers to the physical, chemical, and conformational stability of FGF-18 in the formulations according to the present invention (and including maintenance of biological potency). Instability of a protein formulation may be caused by chemical degradation or aggregation of the protein molecules to form higher order polymers, deglycosylation, modification of glycosylation, oxidation or any other structural modification that reduces at least one biological activity of an FGF-18 protein of the present invention.

The term "stable" solution or formulation, as used herein, is one solution or formulation wherein the degree of degradation, modification, aggregation, loss of biological activity and the like, of proteins therein is acceptably controlled, and does not increase unacceptably with time. Preferably, the formulation retains at least more than 80% of the FGF-18 activity over a period of at least 12 months at room temperature. The stabilized formulation of the present invention comprising FGF-18, has preferably a shelf-life of at least about 12 months, 18 months, more preferably at least 20 months, still more preferably about 24 months, when stored at room temperature. Methods for monitoring the stability of the FGF-18 formulation of the present invention are available in the art, and include the methods described in the examples disclosed herein.

The term "buffer", as used herein, refers to solutions of compounds that are known to be safe in formulations for pharmaceutical or veterinary use and that have the effect of maintaining or controlling the pH of the formulation in the pH range desired for the formulation. Acceptable buffers for controlling pH at a moderately acidic pH to a moderately basic pH include, but are not limited to, phosphate, acetate, citrate, arginine, TRIS, and histidine buffers. "TRIS" refers to 2-amino-2-hydroxymethyl-1,3,-propanediol, and to any pharmacologically acceptable salt thereof. According to the present invention, preferable buffers are phosphate buffers.

The term "surfactant", as used herein, refers to a soluble compound that can be used notably to increase the water solubility of hydrophobic, oily substances or otherwise increase the miscibility of two substances with different hydrophobicities. For this reason, these polymers are commonly used in industrial applications, cosmetics, and pharmaceuticals. They are also used as model systems for drug delivery applications, notably in order to modify the absorption of the drug or its delivery to the target tissues. Well known surfactants include polysorbates (polyoxyethylene derivatives; Tween) as well as poloxamers (i.e. copolymers based on ethylene oxide and propylene oxide, also known as Pluronics®). According to the invention, the preferred surfactant is a poloxamer surfactant and even more preferably is poloxamer 188 (Pluronic® F68).

The term "stabilizing agent", "stabilizer" or "isotonicity agent", as used herein, is a compound that is physiologically tolerated and imparts a suitable stability/tonicity to a formulation. It prevents notably the net flow of water across cell membranes that are in contact with the formulation. During freeze-drying (lyophilisation) process, the stabilizer is also effective as a cryoprotectant. Compounds such as glycerin, are commonly used for such purposes. Other suitable stability agents include, but are not limited to, amino acids or proteins (e.g. glycine or albumin), salts (e.g. sodium chloride), and sugars (e.g. dextrose, mannitol, sucrose and lactose). According to the present invention, the preferred stabilizing agent is a sugar, even more preferably sucrose.

The term "vial" or "container", as used herein, refers broadly to a reservoir suitable for retaining the FGF-18 formulation in lyophilized form. Similarly, it will retain the solvent for reconstitution. Examples of a vial that can be used in the present invention include syringes, ampoules, cartridges, or other such reservoir suitable for delivery of the FGF-18 formulation to the patient via injection, preferably via intraarticular injection. Alternatively, the vial retaining the FGF-18 formulation and the one retaining the solvent for reconstitution can be presented as the 2 compartments of a dual-chamber system (syringe or cartridge for example). Vials suitable for packaging products for intraarticular administration are well known and recognized in the art.

The term "solvent", as used herein, refers to a liquid solvent either aqueous or non-aqueous. The selection of the solvent depends notably on the solubility of the drug compound on said solvent and on the mode of administration. Aqueous solvent may consist solely of water, or may consist of water plus one or more miscible solvents, and may contain dissolved solutes such as sugars, buffers, salts or other excipients. The more commonly used non-aqueous solvents are the short-chain organic alcohols, such as, methanol, ethanol, propanol, short-chain ketones, such as acetone, and poly alcohols, such as glycerol. According to the present invention, the preferred solvent is an aqueous solvent such as water or a saline solvent.

The term "cartilage disorder", as used herein, encompasses disorders resulting from damages due to traumatic injury or chondropathy. Examples of cartilage disorders that may be treated by the administration of the FGF-18 formulation described herein include but are not restricted to, arthritis, such as osteoarthritis or rheumatoid arthritis, and cartilage injury.

The term "Osteoarthritis" is used to intend the most common form of arthritis. It may be caused by the breakdown of cartilage. Bits of cartilage may break off and cause pain and swelling in the joint between bones. Over time the cartilage may wear away entirely, and the bones will rub together. Osteoarthritis can affect any joint but usually concerns hands and weight-bearing joints such as hips, knees, feet, and spine. In a preferred example, the osteoarthritis may be knee osteoarthritis or hip osteoarthritis. The skilled person is fully aware of osteoarthritis classifications that are used in the art, in particular the OARSI assessment system (see for instance Custers et al., 2007). Osteoarthritis is one of the preferred cartilage disorders that can be treated by administering the FGF-18 formulations according to the present invention.

The term "cartilage injury" as used herein is a cartilage disorder or cartilage damage resulting notably from a trauma. Cartilage injuries can occur as a result of traumatic mechanical destruction, notably further to an accident or surgery. Also considered within this definition is sport-related injury or sport-related wear of tissues of the joint.

DETAILED DESCRIPTION OF THE INVENTION

The main object of the present invention is a stable freeze-dried formulation comprising or consisting of an FGF-18 protein, a buffer, a poloxamer surfactant and a sugar as stabilizing agent. In a preferred embodiment, the buffer is a phosphate buffer, the poloxamer surfactant is poloxamer 188, and the stabilizing agent is sucrose. Preferably, the FGF-18 protein is selected from the group consisting of: 1) a polypeptide comprising or consisting of the mature form of human FGF-18, corresponding to the sequence comprising or consisting of residue 28 (Glu) to residue 207(Ala) of SEQ ID NO: 1, 2) a polypeptide comprising or consisting of a truncated form of human FGF-18 comprising or consisting of residue 28 (Glu) to residue 196 (Lys) of SEQ ID NO:1, and 3) a polypeptide comprising or consisting of SEQ ID NO:2. More preferably, FGF-18 is trFGF-18.

The concentration of FGF-18 in the present invention is preferably at or about 20 to 300 mcg/vial, preferably at or about 20, 30, 40, 50, 60, 70, 80, 90, 100, 150, 200, 250 or 300 mcg/vial, even more preferably at or about 20, 30, 60, 100, 200 or 300 mcg/vial. FGF-18 can be added in excess of 5%, in order to prevent protein losses that could occur during formulation. For instance, for an FGF-18 concentration of 30 mcg/vial, the compound can be added in an amount of 31.5 mcg/vial.

Preferably the formulations of the invention retain at least 80% of the FGF-18 biological activity at the time of lyophilisation and/or packaging over a period of at least 12 months (before the first use). FGF-18 activity may be measured as described in the following section "Examples".

Preferable buffers according to the present invention are phosphate buffers, and keep the pH comprised between 6 and 8, preferably comprised between 7 and 7.5, and even more preferably at or about 7.2.

Buffer concentration in total solution is preferably at or about 5 to 500 mM. In a preferred embodiment, the concentration of the buffer is at or about 10 to 100 mM. Preferably, the concentration of the buffer is at or about 10 mM.

The stabilizing agent in the present invention is preferably a sugar. The preferred sugar is sucrose. Preferably, the concentration of the stabilizing agent is at or about 0.5 to 250 mg/vial, more preferably at or about 1 to 100 mg/vial, more particularly at or about 15 to 60 mg/vial, even most preferably at or about 30 mg/vial.

The surfactant according to the present invention is preferably a poloxamer surfactant, and in particular is poloxamer 188 (i.e. Pluronic® F68). Preferably the concentration of surfactant is at or about 0.01 to 10 mg/vial, more preferably at or about 0.05 to about 5 mg/vial, more particularly at or about 0.1 to about 1 mg/vial, even most preferably at or about 0.1, 0.2 or 0.4 mg/vial, and in particular at or about 0.2 mg/vial.

In a preferred embodiment, the stable freeze-dried formulation in the present invention comprises or consists of FGF-18 at or about 20, 30, 60, 100, 200 or 300 mcg/vial, 10 mM phosphate buffer at pH 7.2, 30 mg/vial of sucrose and 0.2 mg/vial of poloxamer 188. When a 5% overage is included, the freeze-dried formulation according to the present invention comprises FGF-18 at or about 21, 31.5, 63, 105, 210 or 315 mcg/vial.

In a further embodiment, the present invention is directed to a stable freeze-dried formulation comprising:
1) FGF-18:sucrose at a concentration ratio from or about 1:95000 to or about to 1:6000, preferably at or about 1:92000, 1:61000, 1:31000, 1:18450, 1:9200 or 1:6100,
2) FGF-18:poloxamer 188 at a concentration ratio from or about or 1:25 to or about to 6:10, preferably at or about 1:25, 5:83, 5:42, 1:5, 2:5 or 6:10,
3) FGF-18:phosphate buffer at pH 7.2 at a molar ratio from or about or 1:10500 to or about to 1:700, preferably at or about 1:10500, 1:7000, 1:3500, 1:2100, 1:1050 or 1:700, wherein the FGF-18 protein is preferably selected from the group consisting of: 1) a polypeptide comprising or consisting of the amino acid residues 28 (Glu)-207(Ala) of SEQ ID NO:1, 2) a polypeptide comprising or consisting of the amino acid residues 28 (Glu)-196 (Lys) of SEQ ID NO:1, or 3) a polypeptide comprising or consisting of SEQ ID NO:2. More preferably, the FGF-18 protein comprises or consists of the amino acid residues 28 (Glu)-207(Ala) of SEQ ID NO:1.

In yet another embodiment, the present invention is directed to a stable freeze-dried formulation comprising:
1) FGF-18:sucrose at a molar ratio from or about 1:90000 to or about to 1:5000, preferably at or about 1:87000, 1:58000, 1:29000, 1:17400, 1:8700 or 1:5800,
2) FGF-18:poloxamer 188 at a molar ratio from or about or 5:120 to or about to 5:8, preferably at or about 5:118, 5:79, 10:79, 10:47, 5:12 or 5:8,
3) FGF-18:phosphate buffer at pH 7.2 at a molar ratio from or about or 1:10000 to or about to 1:700, preferably at or about 1:10000, 1:6600, 1:3300, 1:2000, 1:1000 or 1:700, wherein the FGF-18 protein is preferably selected from the group consisting of: 1) a polypeptide comprising or consisting of the amino acid residues 28 (Glu)-207(Ala) of SEQ ID NO:1, 2) a polypeptide comprising or consisting of the amino acid residues 28 (Glu)-196 (Lys) of SEQ ID NO:1, or 3) a polypeptide comprising or consisting of SEQ ID NO:2. More preferably, the FGF-18 protein comprises or consists of the amino acid residues 28 (Glu)-196 (Lys) of SEQ ID NO:1. Even more particularly, the FGF-18 protein comprises or consists of SEQ ID NO:2. In a particular embodiment, FGF-18 protein is trFGF-18.

The invention further provides a method for manufacturing any of the above described stable freeze-dried formulations of FGF-18, wherein the method comprises the steps of:
1) forming a mixture of FGF-18 together with a buffer, a poloxamer surfactant and a sugar as a stabilizing agent, and
2) subjecting the mixture to lyophilisation.

Steps 1 and 2 are carried out using conventional procedures. As an example, in order to prepare a suitable stable formulation, a given amount of FGF-18, such as trFGF-18, is mixed with phosphate buffer which keeps the pH at or about 7.2, poloxamer 188 and sucrose. Each of these compounds (i.e. FGF-18, the buffer, the surfactant and the stabilizing agent) can be used according to the concentrations, pH, and/or ratios above described. The resulting mixture is lyophilised and then dispensed into vials. Variations of this process will be recognized by one of ordinary skill in the art.

The invention also provides an article of manufacture, for pharmaceutical or veterinary use, comprising:
1) a first container comprising any of the above described stable freeze-dried formulation, said formulation comprising or consisting of FGF-18, a buffer, a poloxamer surfactant, a sugar as a stabilizing agent, and
2) a second container comprising a solvent for reconstitution.

As an example, the first container comprises a stable freeze-dried formulation comprising or consisting of a given amount of FGF-18, such as trFGF-18, phosphate buffer which keeps the pH at or about 7.2, poloxamer 188 and sucrose, and the second container comprises saline solution (0.9% w/v sodium chloride for injection). Each of these compounds (i.e. FGF-18, the buffer, the surfactant and the stabilizing agent) can be used according to the concentrations, pH, and/or ratios above described. Preferably, the container retaining the FGF-18 formulation and the one retaining the solvent for reconstitution correspond to the two compartments of a dual-chamber system (syringe or cartridge for example).

Also described, a packaging material providing instructions to reconstitute the freeze-dried formulation of FGF-18 (first container) in the solvent (second container).

The freeze-dried formulations of the invention may be kept for at least about 12 months to about 24 months. Under preferred storage conditions, before the first use, the formulations are kept away from bright light (preferably in the dark), at room temperature (at or about 25° C.).

The stable freeze-dried formulation of the invention needs to be reconstituted, preferably under sterile condition, with a solvent, such as water or a saline solution (e.g. 0.9% w/v sodium chloride for injection) prior to use, i.e. prior to injection. After reconstitution, the volume to be injected is preferably from 0.5 mL to 5 mL, more preferably 0.5, 1 or 2 mL. The FGF-18 formulation should be administered preferably within one hour of reconstitution.

The present invention provides stable freeze-dried formulations of FGF-18, in particular for single use, suitable for pharmaceutical or veterinary use.

The stable freeze-dried formulation comprising FGF-18, in the present invention, can be used, after reconstitution, for administration for improving cartilage repair or for the treatment of cartilage disorders, such as osteoarthritis or cartilage injuries.

These stable freeze-dried formulations, after reconstitution, are suitable for use in injection and alternative delivery systems. In a particularly preferred embodiment, the formulations of the invention are for intraarticular injection. They can be administered, after reconstitution, by direct injection into the synovial fluid of the joint or directly into the defect. In a preferred embodiment of the present invention, the intraarticular administration is done in a joint selected from joint of the hip, knee, elbow, wrist, ankle, spine, feet, finger, toe, hand, shoulder, ribs, shoulder blades, thighs, shins, heels and along the bony points of the spine. In yet another preferred embodiment the intraarticular administration is done in the joint of the hip or the knee.

The FGF-18 formulations of the present invention have improved stability, and can be easily stored at room temperature (at or about 25° C.) or at 2-8° C. (see following examples), preferably at room temperature. Indeed, the inventors have found that freeze-dried formulations comprising FGF-18 (e.g. trFGF-18), 10 mM phosphate buffer at pH 7.2, 30 mg/vial of sucrose and 0.2 mg/vial of poloxamer 188 are stable over time, notably when stored at room temperature. Said formulations minimise the loss of active principle, i.e. FGF-18. It has also been found that said formulations are more resistant to oxidation and to formation of protein aggregates.

The following examples are provided to further illustrate the preparation of the formulations and compositions of the invention. The scope of the invention shall not be construed as merely consisting of the following examples.

DESCRIPTION OF THE FIGURE

FIG. 1: Shows the effect of the surfactant (poloxamer 188) on FGF-18 recovery before lyophilization process. Pre-formulations containing 10 mg/ml (+5% overage) FGF-18 in phosphate buffer pH 7.2 were used, while varying the concentration of surfactant (from 0 to 0.2%). The protein content was assessed for each of the pre-formulations before filtration (BF) and after filtration (T=0).

DESCRIPTION OF THE SEQUENCES

SEQ ID NO. 1: Amino acid sequence of the native human FGF-18.

SEQ ID NO. 2: Amino acid sequence of the recombinant truncated FGF-18 (trFGF-18).

EXAMPLES

Material

The recombinant truncated FGF-18 (trFGF-18) of the present examples has been prepared by expression in *E. coli*, according to the technique described in the application WO2006/063362. In the following examples, trFGF-18 and FGF-18 are used interchangeably.

Other substances used in the examples are the following:
Sucrose (1.07653, Merck; Molecular weight: 342.30 g/Mol)
Sodium dihydrogen phosphate monohydrate (1.06345, Merck)
Dihydrate Disodium hydrogen phosphate (1.06586, Merck)
Poloxamer 188 (Lutrol F 68 DAC, USP/NF, Basf; Molecular weight: 8400 g/Mol)
Water for injection,
Saline solution (0.9% w/v sodium chloride for injection)
Monoclonal antibody anti-FGF-18 clone #F5A2, for protein content (Provided by RBM)
BAF3-FGFR3c cells (Washington University)
Roswell Park Memorial Institute (RPMI) 1640 based selective medium (Invitrogen).
ATPlite 1 step luminescence assay system (Perkin Elmer)
Heparin H3149 (Sigma)
Equipment
AMICON ULTRA-4 10,000 cutoff (UFC 8012024, Amicon)
Biacore 2000 (Biacore)
CO2 incubator (Heraeus)
Column TSK2000SWxl, 7.8×300 mm, 5µ (TosoHaas, code 08540)
Guard column TSKG2000 (Hichrom, code 8543)
HPLC systems (Waters)
Luminometer (Perkin Elmer)
Membrane filters 0.22 µm (Durapore type GWVP, Millipore)
Stabileo software (ver. 1.1; package of Microsoft® Excel Visual Basic®)
GraphPad software (Prism)
Stainless steel holders 22 mL and 220 mL capacity (Sartorius)
Zorbax 300SB-C18 (150×4.6 cm) column
DIN2R (3 ml) glass vials (Nuova OMPI)
Coated rubber stoppers (S2F452, D777-1, B2-40, West Pharmaceutical)
Rubber stoppers (code 1779, W1816 grey, Pharma-Gummi)
Methods
Different Assays on Formulations
  Standard methods were used for:
  SE-HPLC,
  RP-HPLC,
  Residual moisture,
  pH,
  Osmolality (Time 0, only),
  SDS-PAGE/SS, and
  Peptide mapping/UPLC (oxidized forms).
Protein Content The quantification of the protein, i.e. trFGF-18, in the different formulations was performed by Biacore. Samples (25 µL) containing trFGF-18 were tested (appropriately diluted in presence of 10 mg/mL of BSA) by flowing, at 5 µL/min at 25° C., over sensor surface, previously coated with the monoclonal antibody anti-FGF-18 clone F5A2, followed by 5 µL of 10 mM Glycine pH 2.0 as regeneration buffer. Reference standard (IRS FGF-18 No. 051230), ranging from 125 up to 2,000 ng/mL, was run in each analytical session. Results were collected as Resonance Unit (RU) and FGF-18 level of each sample was extrapolated from the standard curve fitted using quadratic algorithm with Log transformed data.

Bioassay

The biological activity of FGF-18 is measured as proliferation activity by an in-vitro bioassay using BaF3 cell line stably transfected with the FGF receptor 3c (FGFR3c). BaF3 cells expressing FGFR3c proliferate under the FGF-18 stimuli.

BaF3/FGFR3c cells are cultured in RPMI 1640 based selective medium in the presence of r-hIL-3 as growth factor. In order to specifically test the proliferative effect of FGF-18, cells need to be IL-3 deprived. Therefore, cells are cultured at 37° C., 5% $CO_2$ in the absence of r-hIL-3 for 26 hours before the assay.

Standard and samples are 5-fold serially diluted in assay medium in the range of concentration from 0.002 U/mL up to 177.5 U/mL. IL-3 deprived BAF3/FGFR3c cells (20,000 cells/well) are incubated at 37° C., 5% $CO_2$ with FGF-18 in the presence of 1 µg/mL heparin, and 10% Newborn Calf Serum, and then cell proliferation is assessed after 48 hours by "ATPlite 1 step" luminescence assay, an ATP monitoring system based on Firefly luciferase.

Sample potency is measured applying the extended dose-response curve model. With this model, the whole dose-response curve of standard and samples are fitted by sigmoidal dose-response curve with variable slope (4PL) algorithm reporting cps (i.e. counts per second) values versus log of FGF-18 concentrations. For each curve $EC_{50}$ is automatically calculated by GraphPad software. Sample potency is calculated on the basis of the ratio between the $EC_{50}$ of the reference preparation and that of the unknown sample (potency ratio). The potency of FGF-18 is expressed as U/mL.

Example 1

Freeze-Dried Formulations of trFGF-18

The composition of the FGF-18 freeze-dried formulations is provided in the Table 1 below.

TABLE 1

Composition for FGF-18 freeze-dried formulations (*)

| Formulation No. | Formulation name | FGF-18 (mcg/vial) | Buffer | Sucrose (mg/vial) | Poloxamer 188 (mg/vial) |
|---|---|---|---|---|---|
| 1 | FD-20 | 20 | 10 mM phosphate pH 7.2 | 30 | 0.2 |
| 2 | FD-30 | 30 | 10 mM phosphate pH 7.2 | 30 | 0.2 |
| 3 | FD-60 | 60 | 10 mM phosphate pH 7.2 | 30 | 0.2 |
| 4 | FD-100 | 100 | 10 mM phosphate pH 7.2 | 30 | 0.2 |
| 5 | FD-200 | 200 | 10 mM phosphate pH 7.2 | 30 | 0.2 |
| 6 | FD-300 | 300 | 10 mM phosphate pH 7.2 | 30 | 0.2 |

(*) upon reconstitution with 1 mL WFI (Water For Injection).

Freeze-dried formulations were manufactured as follows: sucrose and Poloxamer 188 were dissolved in the phosphate buffer. Then, the needed amount of drug substance (trFGF- 18) was added, the pH checked and the solution taken to final volume. The solution was then filtered through a 0.22 μm membrane (Durapore®) under nitrogen pressure, maintaining a filtration ratio of about 20 cc/cm² or of about 50 cc/cm².

The final solution was then manually filled, under sterile conditions into glass vials (0.5 mL/vial) and freeze-dried according to the following cycle:

| STEP | Temperature (° C.) | Duration |
|---|---|---|
| Loading | +4 | 15 min |
| Freezing | −25 | 2 hours |
| Freezing | −15 | 1 hour and 40 min |
| Freezing | −45 | 3 hours |
| Primary Drying | −10 | 14 hours |
| Secondary Drying | +35 | 22 hours |

The freeze-dried formulations are ready to be reconstituted, at any time, with a solvent, such as water for injection or a saline solution.

Example 2

Preliminary Stability Studies of FGF-18 Formulations

Example 2.1

Accelerated stability conditions (at 2-8° C., 25° C. and 40° C.) were used in order to identify freeze-dried pre-formulations to be further studied (data not shown).

Various preliminary freeze-dried formulations have been prepared, in order to identify the best candidate formulations. In the frame of this preliminary study, various buffers have been assessed, including phosphate and histidine buffers. Various concentrations of sucrose and poloxamer 188 have also been tested. The pre-candidate formulations were tested for purity (by SE-HPLC and RP-HPLC), protein content (by Biacore), biological activity (in-vitro bioassay), residual moisture, pH and osmolality. Supportive stability data have also been generated by SDS-PAGE/SS (purity) and by peptide mapping/UPLC (oxidized forms).

Example 2.2 (Stability Data for the Preliminary Formulations; Data not Shown)

The stability data collected for the preliminary freeze-dried formulations by SE-HPLC over 3-4 weeks storage indicate that phosphate buffer at pH 7.2 is to be preferred, since much higher purity level (i.e. higher % of monomer) were observed compared to histidine buffer at pH 6 (see table 2). The amount of sucrose (15 mcg/vial vs 30 mcg/vial) plays also a role in stabilizing FGF-18 versus aggregation, where globally higher monomer recoveries were observed with 30 mcg/vial of sucrose (storage at 25° C. and 5° C.). In addition, higher protein recovery was observed after filtration step (before lyophilisation process) as the surfactant (i.e. poloxamer 188) was increased, with best results at 0.2 mg/vial (FIG. 1).

Based on the results from this pre-formulation phase, six freeze-dried formulations were prepared for further investigations (formulations 1-6 from Table 1; also referred as candidate formulations).

Example 3

Stability Studies of FGF-18 Freeze-Dried Formulations

Two weeks to 24 months stability data have been collected on the candidate freeze-dried formulations of Table 1.

Example 3.1 (Purity by SE-HPLC)

The results for the statistical evaluation performed by Stabileo on the stability data generated by SE-HPLC are summarized in Table 3: no significant loss in purity (monomer content) was detected for any freeze-dried candidate formulation upon storage at the different temperatures (up to 6 months at 40° C. and up to 24 months at 25° C.).

Example 3.2 (Purity by SDS-PAGE/SS)

The results generated by SDS-PAGE confirmed purity levels globally higher than 99% for any freeze-dried formulations upon storage at all the tested temperatures (at least 6 months at 40° C. and up to 18 months at 25° C.). The results are provided in Table 4.

Example 3.3 (Purity by RP-HPLC)

The results for the statistical evaluation performed by Stabileo on the stability data generated by RP-HPLC are summarized in Table 5: no significant loss in purity (% main peak) was detected for any freeze-dried candidate formulation upon storage at the different temperatures (up to 6 months at 40° C. and up to 18 months at 25° C.). Therefore, formulating FGF-18 according to the present invention does not result in any loss of purity compared to starting material (pure) FGF-18. It is noted that as the starting material (before formulation) was not completely pure (impurities were not completely resolved by RP-HPLC), the peak before formulation was not at 100%, but for instance at 77.5% for FD-30 and 87.4% for FD-300 and the peak at T=0 was for instance at 76.8% for FD-30 and 87.7% for FD-300.

Example 3.4 (Protein Content Assay)

The results of the protein concentration measured by Biacore are summarized in Tables 6 and 7. No major loss was detected upon filtration through the 0.22 μm membrane, i.e. almost complete protein recovery was observed (see "AF" column in Table 6). Upon reconstitution of the freeze-dried product with 1 mL WFI (see "T0") column in Table 6), a lower recovery was obtained, which can be explained by adsorption of the protein on the glass vial (upon reconstitution, the protein solution is then exposed to a larger surface).

From a stability point of view, no loss in the protein content was detected by Biacore for all strengths at all the tested temperatures, as shown in Table 7 (up to 6 months at 40° C. and up to 24 months at 25° C.).

Example 3.5 (Biological Activity)

Results of the biological activity (expressed in U/container) for all of the freeze-dried candidates upon storage is provided in Table 8. For instance, the biological activity observed for the higher strength (300 mcg/vial of trFGF-18) upon storage, both at 25° C. and 40° C. was stable over time. More variability was observed with the lowest strength FD-20. Since no change in the product stability was detected by any of the other tests, this decrease observed with FD-20 has to be confirmed after 39, 52, 78 and 104 weeks of storage at 25° C.

Example 3.6 (Oxidized Forms)

The level of oxidized forms detected for all strengths upon storage is summarized in Table 9: among the Met residues that could undergo oxidation, the results indicate that Met 1 is more susceptible to oxidation, for all strengths and at any of the assessed temperatures.

Example 3.7 (Residual Moisture)

No significant increase in the residual moisture occurred upon storage for all strengths; residual moisture values below or about 1% were globally measured throughout the stability study (see Table 10) (up to 6 months at 40° C. and up to 24 months at 25° C.).

Example 3.8 (pH Variation)

No significant pH variation was observed upon storage at any of the tested temperatures, for all strengths (See Table 11) (up to 6 months at 40° C. and up to 24 months at 25° C.).

Example 3.9 (Osmolality Variation)

No significant osmolality variation was observed upon storage at any of the tested temperatures, for all strengths (See Table 12) (up to 6 months at 40° C. and up to 24 months at 25° C.).

Tables

TABLE 2

Percentage (%) of FGF-18 monomers in freeze-dried pre-formulations (10 mcg/vial of FGF-18 and 0.2 mg/vial of F68) upon storage, analyzed by SE-HPLC

| Composition | 40° C. | | 25° C. | | 5° C. | |
|---|---|---|---|---|---|---|
| | 3 w | 4 w | 3 w | 4 w | 3 w | 4 w |
| histidine buffer pH 6; F68; 30 mg/vial sucrose | 81.6 | 71.9 | 78.2 | 75.5 | 82.3 | 83 |
| phosphate buffer pH 7; F68; 30 mg/vial sucrose | 88.1 | 90 | 89.4 | 91.2 | 96.5 | 93.4 |

TABLE 3

Percentage (%) of FGF-18 monomers in the freeze-dried candidate formulations upon storage, analyzed by SE-HPLC.

| 40° C. | | | | | |
|---|---|---|---|---|---|
| | T = 0 | 4 w | 8 w | 13 w | 26 w |
| FD-300 | 99.9 | 99.9 | 99.9 | 99.9 | 99.9 |
| FD-30 | 100.0 | 99.7 | 99.8 | 99.8 | 99.8 |

| 25° C. | | | | | | | |
|---|---|---|---|---|---|---|---|
| | T = 0 | 13 w | 26 w | 39 w | 52 w | 78 w | 102 w |
| FD-300 | 100.0 | 99.9 | 100.0 | 99.9 | 100.0 | 99.9 | 100.0 |
| FD-30 | 100.0 | 99.8 | 99.8 | 100.0 | 99.8 | 99.4 | 100.0 |

| 2-8° C. | | | | | | | |
|---|---|---|---|---|---|---|---|
| | T = 0 | 4 w | 8 w | 13 w | 26 w | 39 w | 52 w | 78 w |
| FD-30 | 100.0 | 100.0 | 100.0 | 98.8 | 99.8 | 99.7 | 99.5 | 99.7 |

TABLE 4

Purity of the FGF-18 freeze-dried candidate formulations upon storage, analyzed by SDS-Page (in %).

| 40° C. | | | | |
|---|---|---|---|---|
| | 2 Mo | 6 Mo | 7 Mo | 9 Mo |
| FD-300 | >99.5 | >99.0 | — | — |
| FD-30 | — | — | >97.5 | 99.0 |

| | 7 Mo | 9 Mo | 12 Mo | 18 Mo |
|---|---|---|---|---|
| | 25° C. | | | |
| FD-300 | >97.5 | >99.5 | >99.0 | >99.5 |
| FD-30 | >99.0 | 99.0 | >99.0 | >99.0 |
| | 2-8° C. | | | |
| FD-30 | >97.5 | 99.0 | >99.0 | >99.0 |

TABLE 5

Purity of the FGF-18 freeze-dried candidate formulations, upon storage, analyzed by RP-HPLC.

| 40° C. | | | | | | |
|---|---|---|---|---|---|---|
| | | T = 0 | 4 w | 8 w | 13 w | 26 w |
| FD-300[a] | % of the main peak | 87.7 | 87.4 | 87.4 | 87.5 | 87.3 |
| | % compared to T = 0 | 100.0% | 99.7% | 99.7% | 99.8% | 99.5% |
| FD-30[b] | % of the main peak | 76.8 | 76.4 | 76.5 | 77.7 | 78.8 |
| | % compared to T = 0 | 100.0% | 99.5% | 99.6% | 101.2% | 102.6% |

TABLE 5-continued

Purity of the FGF-18 freeze-dried candidate formulations, upon storage, analyzed by RP-HPLC.

|  |  | T = 0 | 4 w | 8 w | 13 w | 26 w | 36 w | 52 w | 78 w |
|---|---|---|---|---|---|---|---|---|---|
| 25° C. | | | | | | | | | |
| FD-300[a] | % of the main peak | 87.7 | 87.7 | 87.7 | 87.6 | 87.1 | 87.6 | 87.5 | 87.2 |
|  | % compared to T = 0 | 100.0% | 100.0% | 100.0% | 99.9% | 99.3% | 99.9% | 99.8% | 99.4% |
| FD-30[b] | % of the main peak | 76.8 | 76.7 | 76.7 | 77.1 | 78.8 | 78.4 | 77.5 | 78.6 |
|  | % compared to T = 0 | 100.0% | 99.9% | 99.9% | 100.4% | 102.6% | 102.1% | 100.9% | 102.3% |
| 2-8° C. | | | | | | | | | |
| FD-30[b] | % of the main peak | 76.8 | 77.1 | 76.3 | 77.5 | 77.6 | 78.5 | 77.3 | 78.6 |
|  | % compared to T = 0 | 100.0% | 100.4% | 99.3% | 100.9% | 101.0% | 102.2% | 100.7% | 102.3% |

[a]The peak before formulation was at 87.4%
[b]The peak before formulation was at 77.5%

TABLE 6

FGF-18 recovery upon filtration/filling, analyzed by Biacore.

|  | FGF-18 conc. (mcg/mL) | | | Recovery (%)** | |
|---|---|---|---|---|---|
|  | BF | AF | T0* | AF | Overall |
| FD-30 | 55.6 | 56.1 | 26.4 | 100.9 | 95.1 |

BF = before filtration;
AF = after filtration;
T0 = in the vial
*After reconstitution with 1 mL WFI, the original batch was in 0.5 mL
**% of recovery; compared to the amount of FGF-18 protein in the formulations BF.

TABLE 7

FGF-18 recovery upon storage, based on assay by Biacore (in the freeze-dried candidate formulations).

| 40° C. | | | | | | |
|---|---|---|---|---|---|---|
|  |  | T = 0 | 4 w | 8 w | 13 w | 26 w |
| FD-300 | mcg/mL | 293.5 | 298.9 | 325.9 | 288.7 | 296.7 |
|  | % compared to T = 0 | 101.2% | 103.1% | 112.4% | 99.6% | 102.3% |
| FD-200 | mcg/mL | 198.6 | 195.1 | 198.8 | 187.1 | 191.9 |
|  | % compared to T = 0 | 100.0% | 98.2% | 100.1% | 94.2% | 96.6% |
| FD-60 | mcg/mL | 58.8 | 56.8 | 59 | 58.1 | 55.2 |
|  | % compared to T = 0 | 100.0% | 96.6% | 100.3% | 98.8% | 93.9% |
| FD-30 | mcg/mL | 27.3 | 28.1 | 29.6 | 27.6 | 27.5 |
|  | % compared to T = 0 | 100.0% | 102.9% | 108.4% | 101.1% | 100.7% |
| FD-20 | mcg/mL | 18.7 | 18.6 | 18.4 | 18.6 | 18.7 |
|  | % compared to T = 0 | 100% | 99% | 98% | 99% | 100% |

| 25° C. | | | | | | |
|---|---|---|---|---|---|---|
|  |  | T = 0 | 13 w | 26 w | 39 w | 52 w | 78 w |
| FD-300 | mcg/mL | 293.5 | 274.5 | 296.3 | 299.4 | 281.2 | 290.8 |
|  | % compared to T = 0 | 100.0% | 93.5% | 101.0% | 102.0% | 95.8% | 99.1% |
| FD-200 | mcg/mL | 198.6 | 193.2 | 189.7 | 181.7 | 192.5 | — |
|  | % compared to T = 0 | 100.0% | 97.3% | 95.5% | 91.5% | 96.9% | — |

TABLE 7-continued

FGF-18 recovery upon storage, based on assay by Biacore
(in the freeze-dried candidate formulations).

| | | | | | | | |
|---|---|---|---|---|---|---|---|
| FD-60 | mcg/mL | 58.8 | 58.1 | 57.3 | 54 | 56.9 | — |
| | % compared to T = 0 | 100.0% | 98.8% | 97.4% | 91.8% | 96.8% | — |
| FD-30 | mcg/mL | 27.3 | 28.1 | 27.7 | 26.7 | 27.7 | — |
| | % compared to T = 0 | 100.0% | 102.9% | 101.5% | 97.8% | 101.5% | — |
| FD-20 | mcg/mL | 18.7 | 18.5 | 18.5 | 19.8 | 18.4 | 18.5 |
| | % compared to T = 0 | 100.0% | 98.9% | 98.9% | 105.9% | 98.4% | 98.9% |

2-8° C.

| | | T = 0 | 4 w | 8 w | 13 w | 26 w | 39 w | 52 w |
|---|---|---|---|---|---|---|---|---|
| FD-30 | mcg/mL | 26.4 | 27.2 | 29.5 | 28.6 | 27.4 | 26 | 27.4 |
| | % compared to T = 0 | 100.0% | 103.0% | 111.7% | 108.3% | 103.8% | 98.5% | 103.8% |

TABLE 8

Biological activity of trFGF-18 in the freeze-dried candidate
formulations, upon storage, in Bioassay (U/container)

40° C.

| | | T = 0 | 4 w | 8 w | 13 w | 26 w |
|---|---|---|---|---|---|---|
| FD-300 | Biological activity | 468680 | 544646 | 483078 | 499936 | 539552 |
| | % compared to T = 0 | 100.0% | 116.2% | 103.1% | 106.7% | 115.1% |
| FD-200 | Biological activity | 290000 | 320000 | 360000 | 300000 | 260000 |
| | % compared to T = 0 | 100.0% | 110.3% | 124.1% | 103.4% | 89.7% |
| FD-60 | Biological activity | 90000 | 100000 | 100000 | 100000 | 80000 |
| | % compared to T = 0 | 100% | 111% | 111% | 111% | 89% |
| FD30 | Biological activity | 49000 | 44000 | 45000 | 46000 | 37000 |
| | % compared to T = 0 | 100.0% | 90% | 92% | 94% | 76% |
| FD-20 | Biological activity | 33170 | 29334 | 34030 | 30604 | 26569 |
| | % compared to T = 0 | 100.0% | 88.4% | 102.6% | 92.3% | 80.1% |

25° C.

| | | T = 0 | 13 w | 26 w | 39 w | 52 w | 78 w |
|---|---|---|---|---|---|---|---|
| FD-300 | Biological activity | 468680 | 472222 | 507038 | 520000 | 450000 | 580000 |
| | % compared to T = 0 | 100.0% | 100.8% | 108.2% | 110.9% | 96.0% | 123.8% |
| FD-200 | Biological activity | 290000 | 300000 | 260000 | 240000 | 390000 | — |
| | % compared to T = 0 | 100.0% | 103.4% | 89.7% | 82.8% | 134.5% | — |
| FD-60 | Biological activity | 90000 | 110000 | 90000 | 110000 | 110000 | — |
| | % compared to T = 0 | 100.0% | 122.2% | 100.0% | 122.2% | 122.2% | — |
| FD-30 | Biological activity | 49000 | 43000 | 36000 | 45000 | 48000 | — |
| | % compared to T = 0 | 100.0% | 87.8% | 73.5% | 91.8% | 98.0% | — |
| FD-20 | Biological activity | 33170 | 29586 | 27487 | 32000 | 26000 | 27000 |
| | % compared to T = 0 | 100.0% | 89.2% | 82.9% | 96.5% | 78.4% | 81.4% |

TABLE 9

Oxidized forms of FGF-18, in the freeze-dried candidate formulations upon storage (in %)

|  |  | Met 1 | | Met 116 | | Met 149 | | Met 84 | |
| --- | --- | --- | --- | --- | --- | --- | --- | --- | --- |
|  |  | +25° C. | +40° C. | +25° C. | +40° C. | +25° C. | +40° C. | +25° C. | +40° C. |
| FD-300 | T = 0 | 2.04 | 2.04 | 0.36 | 0.36 | 1.97 | 1.97 | 0.43 | 0.43 |
|  | 4 w | — | 1.60 | — | 0.21 | — | 0.99 | — | 0.19 |
|  | 8 w | — | 1.43 | — | 0.92 | — | 1.20 | — | 0.48 |
|  | 13 w | 1.28 | 1.35 | 0.16 | 0.18 | 0.83 | 0.93 | 0.64 | 0.65 |
|  | 26 w | 1.62 | 1.67 | 0.20 | 0.19 | 1.25 | 1.30 | 0.52 | 0.52 |
| FD-20 | T = 0 | 1.64 | 1.64 | 0.17 | 0.17 | 1.25 | 1.25 | 0.20 | 0.20 |
|  | 4 w | — | 2.16 | — | 0.13 | — | 2.22 | — | 0.19 |
|  | 8 w | — | 1.95 | — | 0.21 | — | 2.86 | — | 0.86 |
|  | 13 w | 2.48 | 2.17 | 0.18 | 0.18 | 2.68 | 2.18 | 0.72 | 0.57 |
|  | 26 w | 2.29 | 2.78 | 0.28 | 0.19 | 1.97 | 2.73 | 0.48 | 0.65 |

TABLE 10

Residual moisture in the FGF-18 freeze-dried candidate formulations, upon storage (in %)

| 40° C. | | | | | |
| --- | --- | --- | --- | --- | --- |
|  | T = 0 | 4 w | 8 w | 13 w | 26 w |
| FD-300 | 1 | 0.7 | 0.6 | 0.8 | 1.1 |
| FD-200 | 1.0 | 0.7 | 0.7 | 0.8 | 1.3 |
| FD-60 | 0.8 | 0.8 | 0.7 | 0.8 | 1.3 |
| FD-30 | 0.8 | 0.7 | 0.9 | 0.5 | 1.2 |
| FD-20 | 0.9 | 1.1 | 0.7 | 0.8 | 1.1 |

| 25° C. | | | | | | |
| --- | --- | --- | --- | --- | --- | --- |
|  | T = 0 | 13 w | 26 w | 39 w | 52 w | 78 w | 104 w |
| FD-300 | 1 | 1 | 1 | 0.3 | 0.8 | 0.8 | 1 |
| FD-200 | 1.0 | 0.7 | 1.0 | 0.8 | 0.7 | — | — |
| FD-60 | 0.8 | 0.8 | 1.0 | 0.9 | 0.7 | — | — |
| FD-30 | 0.8 | 0.7 | 0.7 | 1 | 0.9 | 0.9 | 1 |
| FD-20 | 0.9 | 0.8 | 0.8 | 0.8 | 0.8 | 1.0 | — |

TABLE 11 pH values of the FGF-18 freeze-dried candidate formulations, upon storage

| 40° C. | | | | | |
| --- | --- | --- | --- | --- | --- |
|  | T = 0 | 4 w | 8 w | 13 w | 26 w |
| FD-300 | 7.1 | 7.1 | 7.1 | 7.1 | 7.1 |
| FD-200 | 7.0 | 7.1 | 7.1 | 7.1 | 7.1 |
| FD-60 | 6.9 | 6.9 | 6.9 | 7.0 | 7.0 |
| FD-30 | 7.1 | 7.1 | 7.1 | 7.1 | 7.1 |
| FD-20 | 7.1 | 7.2 | 7.2 | 7.2 | 7.2 |

| 25° C. | | | | | | |
| --- | --- | --- | --- | --- | --- | --- |
|  | T = 0 | 13 w | 26 w | 39 w | 52 w | 78 w | 104 w |
| FD-300 | 7.1 | 7.1 | 7.1 | 7.0 | 7.1 | 7.1 | 7.1 |
| FD-200 | 7.0 | 7.1 | 7.1 | 7.1 | 7.0 | — | — |
| FD-60 | 6.9 | 7.0 | 6.9 | 6.9 | 6.9 | — | — |
| FD-30 | 7.1 | 7.1 | 7.1 | 7.1 | 7 | 7.1 | 7.1 |
| FD-20 | 7.1 | 7.2 | 7.2 | 7.2 | 7.1 | 7.1 | — |

TABLE 12

Osmolality of the FGF-18 freeze-dried candidate formulations, upon storage

| 40° C. | | | | | |
| --- | --- | --- | --- | --- | --- |
|  | T = 0 | 4 w | 8 w | 13 w | 26 w |
| FD-300 | 404.7 | 403 | 393 | 404.3 | 397.7 |
| FD-200 | 342 | 337 | 335 | 342 | 345 |
| FD-60 | 343 | 343 | 335 | 341 | 342 |
| FD-30 | 399 | 403 | 398 | 400 | 388 |
| FD-20 | 343.7 | 337.3 | 336.7 | 345.3 | 341.7 |

| 25° C. | | | | | | |
| --- | --- | --- | --- | --- | --- | --- |
|  | T = 0 | 13 w | 26 w | 39 w | 52 w | 78 w | 104 w |
| FD-300 | 404.7 | 405.7 | 395.7 | 396.7 | 401 | 393.3 | 403 |
| FD-200 | 342 | 342 | 344 | 343 | 331 | — | — |
| FD-60 | 343 | 342 | 343 | 344 | 332 | — | — |
| FD-30 | 399 | 399 | 382 | 394 | 394 | 403 | 389 |
| FD-20 | 343.7 | 352 | 342 | 340 | 350.3 | 342.7 | — |

REFERENCES

1. Ellsworth et al., 2002, Osteoarthritis and Cartilage, 10: 308-320
2. Shimoaka et al., 2002, JBC 277(9):7493-7500
3. WO2008023063
4. WO2004032849
5. WO00/21548
6. WO2008/121563
7. WO92/01442
8. WO01/39788
9. WO98/16644
10. WO2006/063362
11. Custers et al., 2007, Osteoarthritis and Cartilage, 15:1241-1248

The invention claimed is:

1. A freeze-dried formulation comprising fibroblast growth factor 18 (FGF-18), a buffer, a poloxamer surfactant and a sugar as stabilizing agent, wherein the buffer is a phosphate buffer at a concentration at or about 5 to 100 mM and maintains the pH between 7.0 and 7.5, the poloxamer surfactant is poloxamer 188 at a concentration at or about 0.1 to 0.4 mg/vial and the sugar is sucrose at a concentration at or about 10 to 60 mg/vial.

2. The freeze-dried formulation according to claim 1, wherein the phosphate buffer maintains the pH at or about 7.2.

3. The freeze-dried formulation according to claim 1, wherein the concentration of the buffer is at or about 10 to 100 mM.

4. The freeze-dried formulation according to claim 1, wherein the concentration of FGF-18 is at or about 20 to 300 mcg/vial.

5. The freeze-dried formulation according to claim 1, wherein the concentration of the stabilizing agent is at or about 15 to 60 mg/vial.

6. The freeze-dried formulation according to claim 1, wherein the concentration of FGF-18 is at or about 30 mcg/vial.

7. The stable-freeze-dried formulation according to claim 1, wherein the formulation comprises 10 mM phosphate buffer having a pH at or about 7.2, 30 mg/vial of sucrose, 0.2 mg/vial of poloxamer 188 and 20 to 300 mcg/vial of FGF-18.

8. The freeze-dried formulation according to claim 1, wherein the formulation further comprises a 5% overage of FGF-18.

9. The freeze-dried formulation according to claim 1, wherein FGF-18 is selected from the group consisting of:
a) a polypeptide comprising or consisting of the amino acid residues 28-207 of SEQ ID NO:1;
b) a polypeptide comprising or consisting of the amino acid residues 28-196 of SEQ ID NO:1; and
c) a polypeptide comprising or consisting of SEQ ID NO:2.

10. An article of manufacture comprising a first container comprising the stable-freeze-dried formulation according to claim 1 and a second container comprising a solvent for reconstitution.

11. The article of manufacture according to claim 10, wherein the container comprising the freeze-dried formulation and the one comprising a solvent for reconstitution are the two compartments of a dual-chamber system.

12. The freeze-dried formulation of claim 1, wherein the formulation retains at least 80% of the FGF-18 activity over a period of 12 months when stored at room temperature.

* * * * *